(12) United States Patent
Pernot et al.

(10) Patent No.: US 10,172,527 B2
(45) Date of Patent: Jan. 8, 2019

(54) METHOD AND APPARATUS FOR MEASURING A PHYSICAL PARAMETER IN MAMMAL SOFT TISSUES BY PROPAGATING SHEAR WAVES

(75) Inventors: Mathieu Pernot, Paris (FR); Mickael Tanter, Bagneux (FR); Mathieu Couade, Aix en Provence (FR); Jean-Luc Gennisson, Cergy (FR); Mathias Fink, Meudon (FR)

(73) Assignees: Supersonic Imagine, Aix en Provence (FR); Centre National de la Recherche Scientifique—CNRS, Paris (FR); Institut National De La Santé Et De La Recherche Médicale, Paris (FR); Université Paris Diderot-Paris 7, Paris (FR)

(*) Notice: Subject to any disclaimer, the term of this patent is extended or adjusted under 35 U.S.C. 154(b) by 287 days.

(21) Appl. No.: 12/533,546

(22) Filed: Jul. 31, 2009

(65) Prior Publication Data

US 2011/0028838 A1 Feb. 3, 2011

(51) Int. Cl.

| A61B 8/00 | (2006.01) |
|---|---|
| A61B 5/021 | (2006.01) |
| A61B 5/00 | (2006.01) |
| A61B 5/01 | (2006.01) |
| A61B 5/02 | (2006.01) |

(Continued)

(52) U.S. Cl.
CPC .......... *A61B 5/021* (2013.01); *A61B 5/0048* (2013.01); *A61B 5/015* (2013.01); *A61B 5/02007* (2013.01); *A61B 8/08* (2013.01); *A61B 8/485* (2013.01); *G01N 29/0672* (2013.01); *A61B 18/0206* (2013.01); *A61B 18/18* (2013.01); *G01N 2291/02475* (2013.01); *G01N 2291/02491* (2013.01); *G01N 2291/02827* (2013.01);
(Continued)

(58) Field of Classification Search
USPC ....... 600/407, 412, 437, 438, 442, 444, 450, 600/454, 455, 481, 485; 702/42; 73/575, 73/587, 599
See application file for complete search history.

(56) References Cited

U.S. PATENT DOCUMENTS 6,057,927 A * 5/2000 Levesque et al. ............ 356/432
6,267,728 B1 7/2001 Hayden
(Continued)

FOREIGN PATENT DOCUMENTS

| EP | 1 421 905 A1 | 5/2004 |
|---|---|---|
| EP | 1 927 318 A1 | 6/2008 |

(Continued)

OTHER PUBLICATIONS

Renier et al., "Nonlinear shear elastic moduli in quasi-incompressible soft solids", IEEE 2007.*
(Continued)

*Primary Examiner* — Christopher Cook
(74) *Attorney, Agent, or Firm* — Miller, Matthias & Hull LLP

(57) ABSTRACT

Method for measuring a physical parameter in soft tissues of a mammal, in which a mechanical shear wave is propagated through the soft tissues and observation of the propagation leads to determine values of a shear wave propagation parameter. The physical parameter is computed on the basis of these values.

25 Claims, 2 Drawing Sheets

(51) Int. Cl.
*A61B 8/08* (2006.01)
*G01N 29/06* (2006.01)
*A61B 18/02* (2006.01)
*A61B 18/18* (2006.01)

(52) U.S. Cl.
CPC ............. *G01N 2291/044* (2013.01); *G01N 2291/0422* (2013.01); *G01N 2291/106* (2013.01)

(56) References Cited

U.S. PATENT DOCUMENTS

| | | | |
|---|---|---|---|
| 6,371,912 B1* | 4/2002 | Nightingale et al. | 600/437 |
| 6,764,448 B2* | 7/2004 | Trahey et al. | 600/437 |
| 6,770,033 B1 | 8/2004 | Fink et al. | |
| 7,252,004 B2 | 8/2007 | Fink et al. | |
| 7,374,538 B2 | 5/2008 | Nightingale et al. | |
| 2003/0171672 A1* | 9/2003 | Varghese et al. | 600/420 |
| 2004/0034304 A1 | 2/2004 | Sumi | |
| 2005/0252295 A1 | 11/2005 | Fink et al. | |
| 2006/0136152 A1* | 6/2006 | Takahashi | 702/42 |
| 2006/0173319 A1* | 8/2006 | Sumi | 600/437 |
| 2007/0282202 A1* | 12/2007 | Maurice et al. | 600/438 |
| 2008/0214961 A1 | 9/2008 | Matsumoto et al. | |
| 2009/0118615 A1 | 5/2009 | Kato et al. | |
| 2009/0163805 A1* | 6/2009 | Sunagawa et al. | 600/438 |
| 2009/0216119 A1 | 8/2009 | Fan et al. | |
| 2010/0220901 A1* | 9/2010 | Matsumura | 382/128 |
| 2010/0249620 A1* | 9/2010 | Cho | A61B 5/02007 600/504 |
| 2012/0278005 A1 | 11/2012 | Sumi | |

FOREIGN PATENT DOCUMENTS

| | | |
|---|---|---|
| WO | 2005074804 A1 | 8/2005 |
| WO | WO 2005/074804 A1 | 8/2005 |
| WO | WO 2007063916 A1 * | 6/2007 |
| WO | WO2008139245 | 11/2008 |

OTHER PUBLICATIONS

Gennieson et al., "Acoustoelasticity in soft solids: Assessment of the nonlinear shear modulus with the acoustic radiation force", Acoustical Society of America, 2007.*

Ulfhammer, "Impairment of Endothelial Thromboprotective Function by Haemodynamic and Inflammatory Stress Implications for hypertensive disease", Clinical Experimental Research Laboratory, Department of Emergency and Cardiovascular Medicine, Sahlgrenska University Hospital/Östra, Institute of Medicine, 2007.*

International Search Report from counterpart application No. PCT/EP2010/056130; Report dated Aug. 5, 2010.

Gennisson, et al. Acoustoelasticity in soft solids: Assessment of the nonlinear shear modulus with the acoustic radiation force, 2007 Acoustical Society of America; 3211-3219.

Tao Wu, et al. Assessment of Thermal Tissue Ablation With MR Elastography, Magnetic Resonance in Medicine 45: 80-87 (2001).

"Acoustoelasticity in soft solids: Assessment of the nonlinear shear modulus with the acoustic radiation force". J.-L. Gennisson,[a)] M. Renier, S. Catheline, C. Barriere, J. Bercoff, M. Tanter, and M. Fink *laboratoire Ondes et Acousrique, ESPCI, CNRS UMR 7587, INSERM, Universite Paris VII*, 10 rue Vouquelin, 75231 Paris cedex 05, France (Received Jul. 4, 2007 ; revised Aug. 28, 2007 ; accepted Aug. 29, 2007).

\* cited by examiner

METHOD AND APPARATUS FOR MEASURING A PHYSICAL PARAMETER IN MAMMAL SOFT TISSUES BY PROPAGATING SHEAR WAVES

FIELD OF THE INVENTION

The invention relates to methods and apparatuses for measuring a physical parameter in mammal soft tissues by propagating shear waves in these soft tissues.

BACKGROUND OF THE INVENTION

Document U.S. Pat. No. 7,252,004 describes how to measure a shear wave propagation parameter (for instance the shear modulus μ) by propagating shear waves in mammal soft tissues, by using an array of ultrasonic transducers to generate the shear waves and to image the propagation of the shear waves.

OBJECTS AND SUMMARY OF THE INVENTION

One objective of the present invention is to propose a new method, which is quick and easy to use, for measuring additional physical parameters in mammal soft tissues by propagating shear waves in this medium.

To this end, according to the invention, a method is provided for measuring a physical parameter in soft tissue of a mammal, said method comprising:
  at least one shear wave propagation parameter measurement wherein a shear wave propagation parameter of said soft tissue (e.g. the shear modulus or other parameters as will be described hereafter) is measured by using an array of ultrasonic transducers during propagation of at least a shear wave in said soft tissue; and
  a physical parameter determining step wherein said physical parameter of the soft tissue is determined, based on at least said shear wave propagation parameter, said physical parameter being either:
    a parameter of non-linearity of elasticity of said soft tissue, said soft tissue being subject to blood pressure and said physical parameter being determined based on:
      several measurements of said shear wave propagation parameter, at different instants corresponding to different pressure values in the soft tissue induced by the cardiac cycle of the mammal,
      and corresponding pressure values in said soft tissue (e.g. blood pressure);
    or a temperature of the soft tissue, said temperature being determined on the basis of a predetermined law linking said shear wave propagation parameter to said temperature.

Thus, this invention takes advantage of the modification of the shear wave propagation as a function of the variation of at least one physical (thermodynamic) property of the medium (e.g pressure, stress, temperature, etc.). Such a variation can be induced externally or internally or caused by a natural biological effect. For example, internal pressure variations of soft tissues can be naturally induced by the cardiac pulsatility, or internal heating source can be generated remotely using focused ultrasound.

In various embodiments of the method of the invention, one may possibly have recourse in addition to one and/or other of the following steps (which can be used either alone or in combination):
  said shear wave propagation parameter which is determined at each shear wave propagation parameter measurement, is selected from shear wave speed, shear modulus, Young's modulus, shear elasticity and shear viscosity;
  the shear wave propagation parameter measurement comprises the following steps:
    a) an excitation step during which an elastic shear wave is generated in the soft tissue;
    b) an observation step during which the propagation of the shear wave is observed in an observation field in the soft tissue, this observation step comprising the following substeps:
      b1) causing the array of transducers to emit into the soft tissue a succession of ultrasound compression waves, the timing of said ultrasound waves being adapted so that at least some of said ultrasound waves penetrate into the observation field while the shear wave is propagating in the observation field; and
      b2) causing ultrasound signals received from said observation field to be detected in real time by said array of transducers, said ultrasound signals comprising echoes generated by the ultrasound compression wave interacting with reflecting particles in the soft tissue; and
    c) at least one processing step including at least a substep c2) during which:
      c2) at least one movement parameter is determined in the observation field, said movement parameter characterizing movements of said reflecting particles, and a value of said shear wave propagation parameter is determined based on said movement parameter;
    said processing step c) further includes, before said substep c2) of determining said movement parameter, a further substep c1) in which:
      c1) the ultrasound signals received successively from the observation field during substep b2) are processed in order to determine successive propagation images of the shear wave;
    at said substep c2), said movement parameter is determined in at least one predetermined measurement zone in the observation field, by one corresponding transducer which belongs to said transducer array;
    at said substep b1), said ultrasound compression waves are emitted at a rate of at least 300 shots per second.

Another object of the present invention is an apparatus for measuring a physical parameter in soft tissue of a mammal, comprising an array of transducers that are controlled independently by at least one electronic control system adapted:
  to carry out at least one shear wave propagation parameter measurement wherein a shear wave propagation parameter is measured by using said array of ultrasonic transducers during propagation of at least a shear wave in said soft tissue; and
  to determine a physical parameter of the soft tissue, based on at least said shear wave propagation parameter, said physical parameter being either:
    a parameter of non-linearity of elasticity of the soft tissue, said soft tissue being subject to blood pressure and said physical parameter being determined based on:
      several measurements of said shear wave propagation parameter, at different instants corresponding to different pressure values in the soft tissue induced by the cardiac cycle of the mammal and corresponding pressure values in said soft tissue;

or a temperature of the soft tissue, said temperature being determined on the basis of a predetermined law linking said shear wave propagation parameter to said temperature.

In various embodiments of the apparatus of the invention, one may possibly have recourse in addition to one and/or other of the following arrangements (which can be used either alone or in combination):

the electronic control system is adapted:
a) to generate an elastic shear wave in the soft tissue;
b) to observe propagation of the shear wave in an observation field in the soft tissue, by:
b1) causing the array of transducers to emit into the medium a succession of ultrasound compression waves, the timing of said ultrasound waves being adapted so that at least some of said ultrasound waves penetrate into the observation field while the shear wave is propagating in the observation field; and
b2) causing ultrasound signals received from said observation field to be detected in real time by said array of transducers, said ultrasound signals comprising echoes generated by the ultrasound compression wave interacting with reflecting particles in the medium;
c) to process the ultrasound signals received successively from the observation field to determine at least one movement parameter in the observation field, and to determine therefrom a value of said shear wave propagation parameter, said movement parameter characterizing movements of said reflecting particles;

said control system is adapted to determine successive propagation images of the shear wave, and to determine therefrom said movement parameter;

said control system is adapted to determine said movement parameter in at least one predetermined measurement zone in the observation field, based on data coming from one corresponding transducer which belongs to the transducer array;

the control system is adapted to have said ultrasound compression waves emitted at a rate of at least 300 shots per second;

said shear wave propagation parameter which is determined at each shear wave propagation parameter measurement, is selected from shear wave speed, shear modulus $\mu$, Young's modulus E, shear elasticity $\mu_1$, shear viscosity $\mu_2$.

First Aspect of the Invention: Method and Apparatus for Measuring Elasticity of Soft Bilogical Tissue This first aspect of the invention relates to methods and apparatuses for measuring elasticity of soft biological tissue, in particular vascular walls.

BACKGROUND OF THE FIRST ASPECT OF THE INVENTION

Measuring elasticity of blood vessels, in particular arteries, is critical in view of monitoring pathologies like atherosclerosis, i.e. accumulation of atheromatous plaque in the arteries. As a matter of fact, one of the major risks in atherosclerosis is the rupture of the atheromatous plaque.

OBJECTS AND SUMMARY OF THE FIRST ASPECT OF THE INVENTION

One objective of the first aspect of the present invention is to propose a new method for measuring elasticity of soft tissue (in particular vascular walls) which is quick and easy to use.

To this end, according to the first aspect of the invention, a method as defined above is provided, wherein said physical parameter is a parameter of non-linearity of elasticity of the soft tissue, said method comprising:

at least two shear wave propagation parameter measurements at different instants corresponding respectively to two different pressure values in the soft tissue induced by the cardiac cycle; and said physical parameter determining step wherein said parameter of non-linearity of elasticity of the soft tissue is determined, based on at least:
the respective values of the shear wave propagation parameter determined during said shear wave propagation parameter measurements;
and pressure values in said soft tissue, respectively during the shear wave propagation of each shear wave propagation parameter measurement.

Thanks to these dispositions, one obtains easily and quickly a measurement of the fragility of the vascular wall through the parameter of non linearity of elasticity, and thus a measure of the risk of rupture of the atheromatous plaque. Further, the shear wave propagation parameter measurements are non-invasive, and the measurement of blood pressures may also possibly be obtained non-invasively, which may still facilitate the use of the method of the invention.

In various embodiments of the method of the first aspect of the invention, one may possibly have recourse in addition to one and/or other of the following steps (which can be used either alone or in combination):

said soft tissue includes a blood vessel, said shear wave propagation parameter is measured in said blood vessel and said pressure is a blood pressure in said blood vessel;

the parameter of non linearity of elasticity which is determined at the non-linearity determining step d), is the third order shear elastic modulus A;

said shear wave propagation parameter which is determined at each shear wave propagation parameter measurement, is the shear modulus $\mu$, and the third order shear elastic modulus A is determined by solving a set of equations corresponding respectively to the several shear wave propagation measures:

$$A = -12\mu_0 \frac{\mu_0 - \mu(t)}{\sigma(t)}$$

where:
t is the instant when the corresponding shear wave propagation parameter measurement is carried out;
$\mu(t)$ is the value of the shear modulus at instant t;
$\mu_0$ is the value of the shear modulus without constraint;
$\sigma(t)$ is a mechanical stress in the blood vessel at instant t parallel to a direction of polarization of the shear wave, determined on the basis of the pressure in the soft tissue at the place of measurement of the shear wave propagation parameter and at instant t;
said soft tissue includes a blood vessel, said shear wave propagation parameter is measured in said blood vessel and said pressure is a blood pressure in said blood vessel, and the mechanical stress $\sigma(t)$ is determined on the basis of the blood pressure in the blood vessel and on the basis of an image of the blood vessel;
the image of the blood vessel is obtained by echography through said transducer array;

said soft tissue includes a blood vessel, said shear wave propagation parameter is measured in said blood vessel and said pressure is a blood pressure in said blood vessel, and the mechanical stress σ(t) is determined on the basis of the blood pressure in the blood vessel and on the basis of a diameter and a thickness of the vascular wall of the blood vessel;

the pressure (in particular blood pressure) is measured automatically by a pressure sensor, simultaneously to the shear wave propagation parameter measurement;

the blood pressure is measured at a distance from the observation field and then phased to the measurement of the shear wave propagation parameter by taking into account said distance and a pressure wave propagation celerity;

the blood pressure is measured at least at two different characteristic phases of the cardiac cycle, and the measurements of the shear wave propagation parameter are carried out at least at two instants corresponding to said two characteristic phases of the cardiac cycle;

said two characteristic phases of the cardiac cycle are the instants of maximum blood pressure and the instant of minimum pressure;

at the non-linearity determining step, the parameter of non linearity of elasticity is determined at several points of the observation field and a map of said parameter of non linearity of elasticity in the observation field is determined.

Another object of the first aspect of the present invention is an apparatus as defined above wherein said medium is a blood vessel, said physical parameter is a parameter of non-linearity of elasticity of the soft tissue, and said control system is adapted:

to carry out at least two shear wave propagation parameter measurements at different instants; and to determine said parameter of non-linearity of elasticity of the soft tissue, based on at least:

the respective values of the shear wave propagation parameter determined during said shear wave propagation parameter measurements;

and pressure values in said soft tissue, respectively during the shear wave propagation measurements.

In various embodiments of the apparatus of the first aspect of the invention, one may possibly have recourse in addition to one and/or other of the following arrangements (which can be used either alone or in combination):

the parameter of non linearity of elasticity which is determined by said control system, is the third order shear elastic modulus A;

said shear wave propagation parameter which is determined by the control system, is the shear modulus μ, and the control system is adapted to determine the third order shear elastic modulus A by solving a set of equations corresponding respectively to the several shear wave propagation measures:

$$A = -12\mu_0 \frac{\mu_0 - \mu(t)}{\sigma(t)}$$

where:

t is the instant when the corresponding shear wave propagation parameter measurement is carried out;

μ(t) is the value of the shear modulus at instant t;

μ₀ is the value of the shear modulus without constraint;

σ(t) is a mechanical stress in the soft tissue at instant t parallel to a direction of polarization of the shear wave, determined on the basis of the pressure in the soft tissue at the place of measurement of the shear wave propagation parameter and at instant t;

the control system is adapted to measure the pressure in the soft tissue automatically through a pressure sensor, simultaneously to the shear wave propagation parameter measurement;

said soft tissue includes a blood vessel, said shear wave propagation parameter is measured in said blood vessel and said pressure is a blood pressure in said blood vessel, and the control system is adapted to phase the measurement of the blood pressure to the measurement of the shear wave propagation parameter by taking into account:

a distance between a place of measurement of blood pressure and the observation field and then phased said distance, and a pressure wave propagation celerity;

said soft tissue includes a blood vessel, said shear wave propagation parameter is measured in said blood vessel and said pressure is a blood pressure in said blood vessel, and the control system has measures of the blood pressure at least at two different characteristic phases of the cardiac cycle, and is adapted to perform the measurements of the shear wave propagation parameter at least at two instants corresponding to said two characteristic phases of the cardiac cycle;

said two characteristic phases of the cardiac cycle are the instants of maximum blood pressure and the instant of minimum pressure;

the control system is adapted to measure the blood pressure at said characteristic phases of the cardiac cycle;

the control system is adapted to determine the parameter of non linearity of elasticity at several points of the observation field and to determine a map of said parameter of non linearity of elasticity in the observation field.

Second Aspect of the Invention: Method and Apparatus for Measuring the Temperature of Mammal Soft Tissues

FIELD OF THE SECOND ASPECT OF THE INVENTION

This second aspect of the invention relates to methods and apparatuses for measuring the temperature of mammal soft tissues.

BACKGROUND OF THE SECOND ASPECT OF THE INVENTION

Measuring the temperature in mammal soft tissues may be useful for instance in view of better controlling local treatments such as thermal treatments, e.g. by High Intensity Focused Ultrasounds (HIFU) or by radio frequency waves (RF ablation).

OBJECTS AND SUMMARY OF THE SECOND ASPECT OF THE INVENTION

One objective of the second of the present invention is to propose a new method for measuring the temperature of mammal soft tissues, which is quick, easy to use and non invasive.

To this end, according to the invention, a method as defined above is provided, wherein said physical parameter is a temperature of the soft tissue, said temperature being determined on the basis of a predetermined law linking said shear wave propagation parameter to said temperature.

Thanks to these dispositions, one obtains easily, quickly and non-invasively a measurement of the temperature of the soft tissues.

The invention was made possible because the present inventors discovered that shear wave propagation parameters of mammal soft tissues (such as Young's modulus, the shear modulus or viscosity, etc.) are variable with temperature (more particularly at sufficiently high frequencies of the shear wave) and linked to the temperature by a law which can be determined in advance experimentally.

In various embodiments of the method of the second aspect of the invention, one may possibly have recourse in addition to one and/or other of the following steps (which can be used either alone or in combination):
said temperature is determined as a difference between first and second temperatures at two different times;
the temperature is determined at several points of the observation field and a map of said temperature is determined in the observation field.

Another object of the second aspect of the present invention is an apparatus as defined above wherein said physical parameter is a temperature of the soft tissue and said electronic control system is adapted to determine said temperature on the basis of a predetermined law linking said shear wave propagation parameter to said temperature.

In various embodiments of the apparatus of the second aspect of the invention, one may possibly have recourse in addition to one and/or other of the following features (which can be used either alone or in combination):
said temperature is a difference between first and second temperatures at two different times;
said shear waves have at least a frequency which is more than 50 Hz;
the temperature is determined at several points of the observation field and a map of said temperature in the observation field is determined.

BRIEF DESCRIPTION OF THE DRAWING

Other features and advantages of the invention appear from the following detailed description of two embodiments thereof, given by way of non-limiting examples, and with reference to the accompanying drawing.

In the drawings.

MORE DETAILED DESCRIPTION

Figure 1:
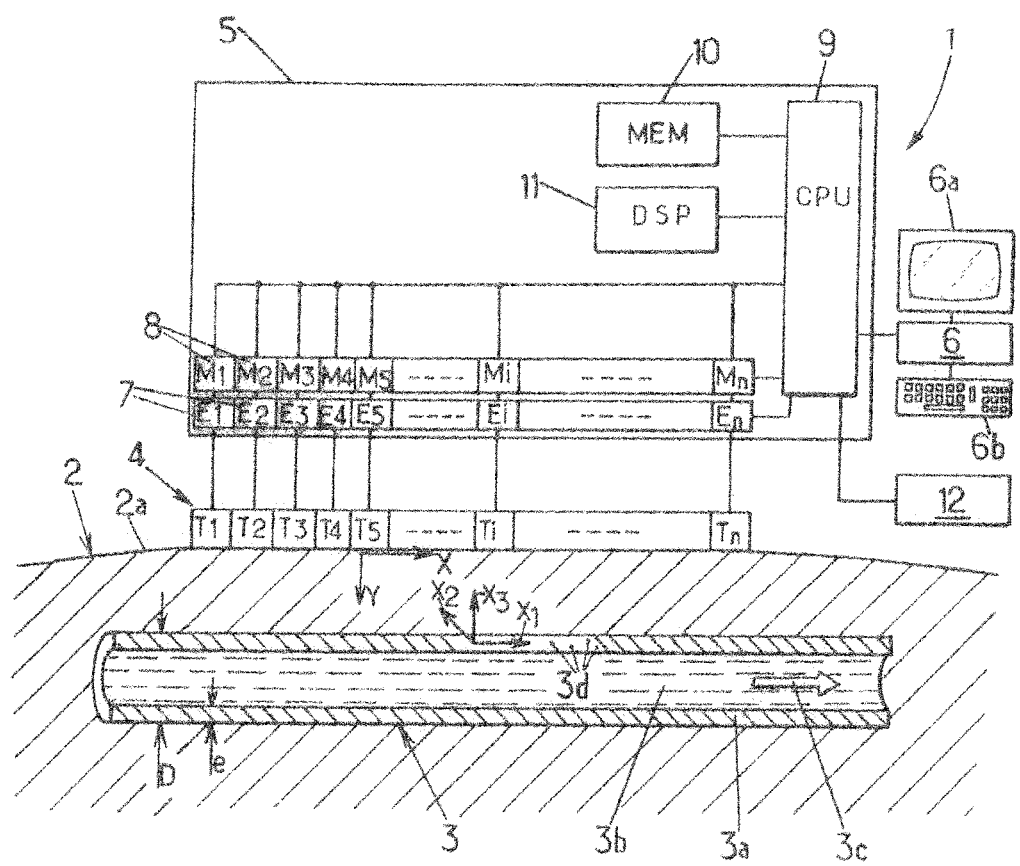
FIG. 1 is a diagrammatic view of a shear-wave imaging device in an embodiment of the first aspect of the invention.

First Aspect of the Invention: Method and Apparatus for Measuring Elasticity of Vascular Walls The apparatus 1 shown on FIG. 1 is adapted for measuring the non linearity of elasticity in an observation field including part of the blood vessel 3 of a living patient 2, more specially an artery.

The vascular wall 3a of the blood vessel 3 can be locally considered as a cylindrical tube of diameter D and of thickness e, in which blood 3b flows in direction 3c. During the cardiac cycle, the blood pressure P(t) in the blood vessel 3 varies between a minimum called the diastolic pressure and a maximum called the systolic pressure. This variation of pressure generates variations in the diameter D of the blood vessel (D may be for instance the external diameter, but could also be the internal diameter or the average of the external and internal diameters) and variations in the tensile stress σ(t) (oriented along an orthoradial axis X2 which is tangent to the point of the vascular wall 3a to be considered, and perpendicular to a longitudinal axis X1 parallel to the longitudinal direction of the blood vessel).

The value of this tensile stress is given by formula (1):

$$\sigma(t) = \frac{P(t) \cdot D}{2e}. \tag{1}$$

The variations of the tensile stress σ(t) also induce variations of the propagation parameters of shear waves in the vascular wall 3a, and these variations are used in the present invention to determine a parameter characterizing the non-linearity of elasticity of the vascular wall, which in turn characterizes the fragility of this vascular wall and in particular the risk of rupture of atheromatous plaque.

In this purpose, the invention provides for a method for measuring elasticity of a vascular wall of a patient's blood vessel, which comprises several shear wave propagation parameter measurements carried out at different instants. Each shear wave propagation parameter measurement is carried out by:
having a mechanical shear wave propagated through the viscoelastic medium constituted by the vascular wall 3a;
observing the propagation of this shear wave in the vascular wall 3a, in particular through reflexion of unfocused ultrasonic compression waves on diffusing particles 3d which are reflective for the ultrasound compression waves and which are naturally contained in biological tissues (the particles 3d may be constituted by any non-uniformity in the vascular wall 3a, and in particular, by particles of collagen);
based on the observation of the shear wave propagation, determining a propagation parameter of shear waves which is representative of elasticity of the vascular wall.

The structure and general way of operation of the apparatus 1 for carrying out this method, has already been described in details in document US-B2-U.S. Pat. No. 7,252,004, and will be recalled hereafter.

The apparatus 1 may include for instance:
an ultrasound transducer array 4, for instance a linear array typically including n ultrasonic transducers $T_1$-$T_n$ juxtaposed along an axis as already known in usual echographic probes (the array 4 is then adapted to perform a bidimensional (2D) imaging of the observation field in a plane X, Y (where X and Y are two axis linked to the array 4, X being parallel to the longitudinal direction of array 4 and Y being perpendicular to the transducers Ti of the array), but the array 4 could also be a bidimensional array adapted to perform a 3D imaging of the observation field); the number n of transducers is more than 1, for instance a few tens (e.g. 100 to 300); the transducers $T_1$-$T_n$ of the array 4 deliver ultrasound compression wave pulses, which pulses are of the type commonly used in echography, for example having a frequency lying in the range 0.5 MHz to 100 MHz, and preferably in the range 0.5 MHz to 15 MHz, e.g. being about 2.5 MHz;

an electronic bay 5 controlling the transducer array 4 and acquiring signals therefrom;

a microcomputer 6 for controlling the electronic bay 5 and viewing ultrasound images obtained from the electronic bay, said computer 6 including for instance a screen 6a and a keyboard 6b or other user interfaces.

The electronic bay 5 and the microcomputer 6 will be referred herein as the control system of the apparatus 1. Such control system might be constituted of more than two devices, or by one single electronic device could fulfill all the functionalities of the electronic bay 5 and of the microcomputer 6.

The electronic bay 5 may include for instance:

n analog/digital converters 7 ($E_1$-$E_n$) individually connected to the n transducers ($T_1$-$T_n$) of the transducer array 4;

n buffer memories 8 ($M_1$-$M_n$) respectively connected to the n analog/digital converters 7;

a central processing unit 9 (CPU) communicating with the buffer memories 8 and the microcomputer 6;

a memory 10 (MEM) connected to the central processing unit 8;

a digital signal processor 11 (DSP) connected to the central processing unit 9.

Besides, in some embodiments of the invention, the central processing unit 9 (or the computer 6) may be connected to an automatic pressure sensor 12 adapted to measure blood pressure of the patient 2, such as:

a sphygmomanometer which measures the blood pressure of the patient in a non-invasive way and transmits a blood pressure signal to the central processing unit 9; and/or a cannula which is inserted in the blood vessel 3 and is fitted with a pressure sensor which measures the blood pressure of the patient in an invasive way and transmits a blood pressure signal to the central processing unit 9.

The transducers $T_1$-$T_n$ are controlled independently of one another by the central processing unit 9. The transducers T1-Tn can thus emit selectively:

either an unfocussed ultrasound compression wave;

or else an ultrasound compression wave that is focused on one or more points of the medium 3.

The wording "unfocussed ultrasound compression wave" as understood herein means any unfocussed wave illuminating the entire observation field in the medium 3, for instance:

an ultrasound compression wave that is "plane" (i.e. a wave whose wave front is rectilinear in the X,Y plane), or any other type of unfocused wave;

a wave generated by causing random ultrasound signals to be emitted by the various transducers $T_1$-$T_n$;

or an ultrasound compression wave that is focused on one or more points of the vascular wall 3a;

or weakly focusing waves (known as "fat" transmit focusing: ratio Focal distance/Aperture>2.5);

or diverging waves such as spherical waves;

or waves focused simultaneously on several focal points;

or more generally any kind of transmit waves that do not correspond to conventional focusing using a single focal point location and a ratio Focal distance/Aperture<2.5.

During operation of the apparatus 1, the transducer array 4 is placed in contact with the skin 2a of the patient 2, over the blood vessel 3 to be studied. The transducer array 4 may be placed in particular transversely or longitudinally to the blood vessel 3, i.e. with the axes X, Y of the transducer array 4 disposed either in a longitudinal plane $X_1, X_2$ which includes the longitudinal axis $X_1$, or in a radial plane $X_2, X_3$ which is perpendicular to the longitudinal axis $X_1$ ($X_3$ is a radial axis which is perpendicular to axes $X_1$, $X_2$ at a point to be studied in the vascular wall 3a). The axis X of the transducer array 4 is disposed substantially parallel to the radial axis $X_3$.

The way of operation of the apparatus 1 is controlled by the control system, i.e. the central processing unit 9 and/or the computer 6, which are programmed for this way of operation.

Observing the Propagation of the Shear Wave

To observe the propagation of the shear wave in the vascular wall 3a, the control system 6, 9 of the apparatus 1 is programmed to perform several steps in succession:

a) an excitation step during which the control system 6, 9 causes an elastic shear wave to be generated in the medium 3 by causing at least one ultrasound wave that is focused in the patient's body to be emitted by the array 4 (this focussed wave may be emitted by all or part of the transducers $T_1$-$T_n$);

b) an observation step during which the propagation of the shear wave is observed simultaneously at a multitude of points of the observation field in the vascular wall 3a, this observation step comprising the following substeps:

b1) the control system 6, 9 causes the array 4 to emit into the viscoelastic medium a succession of unfocused ultrasound compression waves (these unfocussed waves may be emitted by all or part of the transducers $T_1$-$T_n$) at a rate of at least 300 shots per second, for instance at least 500 shots/s (the focusing and the timing of the focussed ultrasound wave emitted in step a), and the timing of said unfocused ultrasound waves are adapted so that at least some of said unfocused ultrasound waves reach the observation field during the propagation of the shear wave through the observation field);

b2) the control system 6, 9 causes the array 4 to detect ultrasound signals received from patient's body 2 (this detection can be carried out by all or part of the transducers of the array 4), said signals comprising echoes generated by the unfocused ultrasound compression wave interacting with the reflecting particles 3d in the observation field, these echoes corresponding (directly or indirectly) to successive images of the displacement of the viscoelastic medium constituting the patient's vascular wall 3a; the detected signals are recorded in real time in the buffer memories $M_1$-$M_n$;

c) at least one processing step during which:

c1) the control system 6, 9 processes the successive ultrasound signals received from the patient's body 2 during substep b2) in order to determine successive propagation images; and c2) the control system 6, 9 determines at least one movement parameter for the viscoelastic medium constituting the patient's vascular wall 3a at various points in the observation field.

It should be noted that the above substep c2) could be omitted: more generally, the method of the invention does not require determining propagation images, and the control system 6, 9 may determine said movement parameter by any other means.

The focused ultrasound wave emitted during the excitation step a) may be a monochromatic wave of frequency f lying in the range 0.5 MHz to 15 MHz, for example being equal to about 2.5 MHz, which is emitted for a duration of k/f seconds, where k is an integer lying in the range 50 to 5000 (e.g. being about 500) and f is expressed in Hz. Such a wave may possibly be emitted during a succession of emission periods separated by rest periods, the emission periods following one another at a rate lying in the range 5 to 1000 emissions per second. The shear wave which is thus created is polarized parallel to axis Y (and thus parallel to axis $X_3$) and propagates parallel to axis X (and thus parallel to axis $X_1$ or $X_2$ or parallel to an axis situated in the plane $X_1, X_2$ according to the orientation of the array 4).

In a variant, the focused ultrasound wave emitted during excitation step a) is a linear combination (in particular a sum) of two monochromatic signals of respective frequencies f1 and f2 such that 20 Hz≤|f1−f2|≤1000 Hz, thus producing an amplitude modulated wave having a modulation frequency |f1−f2|.

In addition, the focused ultrasound wave emitted during excitation step a) may optionally be focused simultaneously or otherwise on a plurality of points so that the shear wave as generated presents a desired wave shape (for example it is thus possible to generate a shear wave that is plane, or on the contrary a shear wave that is focused) and illuminates desired zones in the vascular wall 3a or other parts of the patient's body 2.

During step b1), which may last for example 0.1 to 1 s, it is possible to emit unfocused ultrasound compression waves at a rate lying in the range 500 to 10,000 shots per second, and preferably in the range 1000 to 5000 shots per second (with this rate being limited by the go-and-return travel time for the compression wave through the patient's body 2: it is necessary for all of the echoes that are generated by the compression wave to have been received by the probe 6 before a new compression wave is sent).

Each unfocused ultrasound compression wave propagates through the patient's body 2 at a propagation speed that is much higher than that of shear waves (e.g. about 1500 m/s in the human body), and interacts with the reflecting particles 3d, thereby generating echoes or other analogous disturbances in the signal known in themselves under the name "speckle noise" in the field of echography.

The speckle noise is picked up by the transducers $T_1$-$T_n$ during substep b2), after each shot of an unfocused ultrasound compression wave. The signal $s_{ij}(t)$ as picked up in this way by each transducer $T_i$ after shot No. j is initially sampled at high frequency (e.g. 30 MHz to 100 MHz) and digitized (e.g. on 12 bits) in real time by the analog/digital converter $E_i$ corresponding to transducer $T_i$.

The signal $s_{ij}(t)$ as sampled and digitized in this way is then stored, likewise in real time, in a the buffer memory $M_i$ corresponding to the transducer $T_i$.

By way of example, each memory Mi may present a capacity of about 128 megabytes (MB), and contains all of the signals $s_{ij}(t)$ received in succession for shots j=1 to p.

In deferred time, after all of the signals $s_{ij}(t)$ corresponding to the same propagation of a shear wave have been stored, the central unit 9 processes these signals (or have them processed by another circuit such a summing circuit, or the computer 6 may process the signals itself) using a conventional path-forming step corresponding to substep c1).

This generates signals $S_j(x,y)$ each corresponding to the image of the observation field after shot No. j.

For example, it is possible to determine a signal $S_j(t)$ by the following formula:

$$S_j(t) = \sum_{i=1}^{n} \alpha_i(x, y) \cdot s_{ij}[t(x, y) + d_i(x, y)/V]$$

where:
  $s_{ij}$ is the raw signal perceived by the transducer No. i after ultrasound compression wave shot No. j;
  t(x,y) is the time taken by the ultrasound compression wave to reach the point of the observation field having coordinates (x,y) in the X, Y coordinate system, with t=0 at the beginning of shot No. j;
  $d_i(x,y)$ is the distance between the point of the observation field having coordinates (x,y) and transducer No. i, or an approximation to said distance;
  V is the mean propagation speed of ultrasound compression waves in the viscoelastic medium under observation; and
  $\alpha_i(x,y)$ is a weighting coefficient taking account of apodization relationships (in practice, in numerous cases, it is possible to assume that $\alpha_i(x,y)=1$).

The above formula applies mutatis mutandis when the observation field is three-dimensional (with a two-dimensional array of transducers), with space coordinates (x,y) being replaced by (x,y,z).

After the optional path-forming step, the central unit 9 stores in the central memory M, the image signals $S_j(x,y)$ (or Sj(x) if the image would be in 1 dimension only, or Sj(x,y,z) in case of a 3D image), each corresponding to shot No. j. These signals may also be stored in the computer 6 if the computer itself performs the image processing.

These images are then processed in deferred time in substep c2) by correlation and advantageously by cross-correlation either in pairs, or preferably with a reference image, as explained in US-B2-U.S. Pat. No. 7,252,004.

The above-mentioned cross-correlation can be performed, for example, in the digital signal processor 11, or it may be programmed in the central unit 9 or in the computer 6.

During this cross-correlation process, a cross-correlation function $<S_j(x,y),S_{j+1}(x,y)>$ is maximized in order to determine the displacement to which each particle 3c giving rise to an ultrasound echo has been subjected.

Examples of such cross-correlation calculations are given in US-B2-U.S. Pat. No. 7,252,004.

This produces a set of displacement vectors $\bar{u}(\bar{r},t)$ generated by the shear waves in each position $\bar{r}$ of the vascular wall 3a under the effect of the shear wave (these displacement vectors may optionally be reduced to a single component in the example described herein).

This set of displacement vectors is stored in the memory M or in the computer 6 and can be displayed, for example, in particular by means of the screen 4a of the computer, in the form of a slow motion picture in which the values of the displacements are illustrated by an optical parameter such as a gray level or a color level.

The propagation differences of the shear wave between zones having different characteristics in the vascular wall 3a can thus be seen clearly.

The motion picture of shear wave propagation can also be superposed on a conventional echographic image, which can also be generated by the apparatus 1 described above.

Furthermore, it is also possible to calculate, instead of displacements, the deformations of the vascular wall 3a for each of the points in the observation field, i.e. vectors whose components are the derivatives of the displacement vectors respectively relative to the space variables (X and Y coordinates in the example described). These deformation vectors can be used like the displacement vectors for clearly viewing the propagation of the shear wave in the form of a motion picture, and they also present the advantage of eliminating displacements of the transducer array 4 relative to the patient's body 2 under observation.

Determination of the Shear Wave Propagation Parameter

From the displacement or deformation fields, the computer 6 (or more generally the control system 6, 9) can advantageously then compute at least one propagation parameter of the shear wave, either at certain points (at least 1 point) in the observation field as selected by the user acting on the computer 6, or else throughout the observation field, on the basis of the way in which the movement parameter (displacement or deformation) varies over time in the field of observation X, Y (or X, Y, Z with a two-dimensional array of transducers). When the shear wave propagation parameter is computed at several points in the observation field, the computer 6 may then show a map of said parameter in the observation field, on the screen 6a.

The propagation parameter of the shear wave that is calculated during sub-step c2) is selected, for example, from amongst: the shear modulus μ, or Young's modulus E=3μ, or the propagation speed $c_s$ of shear waves $$\left(c_S = \sqrt{\frac{E}{3\rho}},\right.$$

where ρ is the density of the tissues), or the shear elasticity μ1, as explained in more details in US-B2-U.S. Pat. No. 7,252,004. Such propagation parameter is representative of the elasticity of vascular wall 3a.

This propagation parameter may be computed for instance by the computer 6 (or more generally the control system 6, 9), repeatedly at several different instants (at least at two different instants $t_1$, $t_2$).

For instance, the control system 6, 9 (e.g. the computer 6) may compute the shear modulus μ(t) of the vascular wall 3a at two different instants $t_1$, $t_2$, e. g. at the systole and at the diastole (respectively at the maximum blood pressure and at the minimum blood pressure).

Blood Pressure Measurements

Besides, the blood pressure inside the blood vessel 3 is measured so that the computer 6 (or more generally the control system 6, 9) has values of the blood pressure inside the vessel 3, at the place of the observation field and at said instants of measurement of the shear wave propagation parameter (in the present case, for instance at instants $t_1$, $t_2$).

These values of blood pressure may be obtained for instance by one of the following methods:

a) When the above mentioned pressure sensor 12 is a cannula which is inserted in the blood vessel 3 and is fitted with a pressure sensor which measures the blood pressure of the patient, then this cannula can be inserted in the blood vessel in the vicinity of the transducer array 4, and the values of the blood pressures are automatically measured in real time, simultaneously to the respective observation step (b) of each measurement of the shear wave propagation parameter (i.e. at instants $t_1$ and $t_2$ in the example considered here).

b) When the above mentioned pressure sensor 12 is a an automatic sphygmomanometer which measures the blood pressure of the patient in a non-invasive way, then the measurements of this sphygmomanometer are phased with the measurements of the shear wave propagation parameter in the observation field, to compensate for the differences of phases in the blood pressure cycle between the place of measurement of blood pressure (e.g. on the same artery as the measurement of elasticity but upstream or downstream, or at a finger end of the patient 2).

This phasing may be obtained for instance by measuring both blood pressure and the shear wave propagation parameter at two instants $t_1$ and $t_2$ corresponding respectively to the maximum and minimum of blood pressure (systole and diastole). In this case, the pressure measurement just consists in measuring the maximum and minimum of blood pressure just before or during or just after the shear wave propagation parameter measurements, and the shear wave propagation parameter measurements are done respectively when the diameter D of the blood vessel 3 is maximum (maximum of pressure) and when such diameter D is minimum (minimum of pressure). The diameter of the blood vessel can be automatically monitored by the control system 6, 9, thanks to the imaging capacities of the apparatus 1, so that the control system 6, 9 may phase the shear wave propagation parameter measurements with the maximum and minimum of blood pressure. More generally, the blood pressure may be measured at least at two different characteristic phases of the cardiac cycle, and the measurements of the shear wave propagation parameter are carried out at least at two instants corresponding to said two characteristic phases of the cardiac cycle.

In a variant, the above mentioned phasing may consist in measuring the shear wave propagation parameter and the blood pressure with a time offset Δt which is determined to phase these measurements, specially when blood pressure is measured at a distance from the observation field, for instance on the same artery. Then the phasing can be obtained by applying a time offset Δt between each time t1, t2 of measurement of the shear wave propagation parameter and the time t'1, t'2 of the corresponding blood pressure measurement:

$$t_1 = t'_1 + a.\Delta t \text{ and } t_2 = t'_2 + a.\Delta t \quad (2)$$

$$\Delta t = d/v$$

where:

a=+1 when blood pressure is measured upstream of the observation field of the apparatus 1; a=−1 when blood pressure is measured upstream of the observation field of the apparatus 1;

d is the distance along the artery between the place of measure of blood pressure and the observation field;

v is the celerity of propagation of the pressure wave in the arteries at each heart beat (this celerity v can be either a predetermined value which is memorized in the control system, or v can be measured by the control system thanks to the imaging capacities of the apparatus 1, e.g. by spotting the portion of maximum diameter of the artery and by measuring the celerity of displacement of the zone of maximum diameter along the artery.

c) In a variant, the automatic pressure sensor 12 may be omitted and the blood pressure may just be measured externally to the apparatus 1, for instance by a measurement done by a practitioner with a manual sphygmomanometer: in such a case, the pressure values are entered in the computer 6 (or more generally in the control system 6, 9) and the phasing with the shear wave propagation parameter measurements is obtained in that the shear wave propagation parameter measurements are done respectively when the diameter D of the blood vessel 3 is maximum (maximum of pressure) and when such diameter D is minimum (minimum of pressure).

Determining the Non-Linearity Parameter

The control system 6, 9 (e.g. the computer 6) may then proceed with a non-linearity determining step d) wherein a parameter of non linearity of elasticity is determined based on:
- the respective values of the shear wave propagation parameter determined during said several shear wave propagation parameter measurements (the shear modulus $\mu(t_1)$, $\mu(t_2)$ in the example considered here);
- and the corresponding blood pressure values in said blood vessel (for instance $P(t_1)$, $P(t_2)$ in the present case).

The parameter of non linearity of elasticity which is determined, may be for instance the Landau coefficient called the third order shear elastic modulus A, mentioned for instance by Gennisson et al. (*Acoustoelasticity in soft solids: "Assessment of the non-linear shear modulus with the acoustic radiation force"; J Acoust. Soc. Am* 122 (6), December 2007; p. 3211-3219).

The third order shear elastic modulus A may be determined by the control system by solving a set of equations corresponding respectively to the several shear wave propagation measures:

$$A = -12\mu_0 \frac{\mu_0 - \mu(t)}{\sigma(t)} \qquad (3)$$

where:
t is the instant when the corresponding shear wave propagation parameter measurement is carried out;
$\mu(t)$ is the value of the shear modulus at instant t;
$\mu_0$ is the value of the shear modulus without constraint;
$\sigma(t)$ is the radial mechanical stress in the blood vessel at instant t (i.e. a mechanical stress which is parallel to axis X3, i.e. to the direction of polarization Y of the shear waves), determined on the basis of the blood pressure in the blood vessel at the place of measurement of the shear wave propagation parameter and at instant t as explained above:
$\sigma(t) = P(t)$ (1) in the vascular wall 3a or in a soft tissue situated in the vicinity of the blood vessel, where P(t) is the blood pressure at instant t at the place of measurement of the shear wave propagation parameter (the actual time of measurement of the pressure P may be a time t' different from t, provided the measures are phased so that the pressure measurement corresponds in fact to P(t) as explained above).

When the third order shear elastic modulus A is determined on the basis of two measurements at instants $t_1$ and $t_2$, the control system solves the following system of equations (3) to determine A and $\mu_0$:

$$A = -12\mu_0 \frac{\mu_0 - \mu(t_1)}{\sigma(t_1)} \qquad (3_1)$$

$$A = -12\mu_0 \frac{\mu_0 - \mu(t_2)}{\sigma(t_2)} \qquad (3_2)$$

It should be noted that the parameter of non linearity of elasticity A could also be determined on the basis of another of the above mentioned shear wave propagation parameters, which are linked to the shear modulus $\mu$.

Besides, it should be noted that the parameter of non linearity of elasticity A may be determined at several points of the observation field and a map of said parameter of non linearity of elasticity in the observation field ca be determined by the control system and for instance be shown on the screen 6a of the computer 6.

Finally, instead of computing an image of the vascular wall 3a at substep c1) for determining the movement parameter at substep c2), it would be possible to use the method and apparatus described in document WO-A-2008/139 245 for determining locally said movement parameter in one or several predetermined measurement zone in the observation field, for each measurement zone by one corresponding transducer of the transducer array.

The above description would apply also for measuring the non linearity of elasticity of soft tissues other than vascular walls subject to pressure variations induced by the cardiac cycle, e.g. brain tissues.

Second Aspect of the Invention: Method and Apparatus for Measuring the Temperature of Mammal Soft Tissues The apparatus 1 shown on FIG. 2 is adapted for measuring the temperature of a mammal soft tissue, and more particularly the temperature in an observation field including part of the soft tissues 3' of a living patient 2.

In this purpose, the invention provides for a method for measuring elasticity of a vascular wall of a patient's blood vessel, which comprises at least one shear wave propagation parameter measurement which is carried out by:
- having a mechanical shear wave propagated in the viscoelastic medium constituted by the soft tissues 3';
- observing the propagation of this shear wave in the soft tissues 3', for instance through reflexion of unfocused ultrasonic compression waves on diffusing particles 3d which are reflective for the ultrasound compression waves and which are naturally contained in biological tissues (the particles 3d may be constituted by any non-uniformity in the soft tissues 3', and in particular, by particles of collagen);
- based on the observation of the shear wave propagation, determining a propagation parameter of shear waves in the soft tissues 3'.

The structure and general way of operation of the apparatus 1 for carrying out this method, has already been described in details in document US-B2-U.S. Pat. No. 7,252,004, and has already been recalled above for the first aspect of the invention and will not be described again for the second aspect of the invention.

Figure 2:
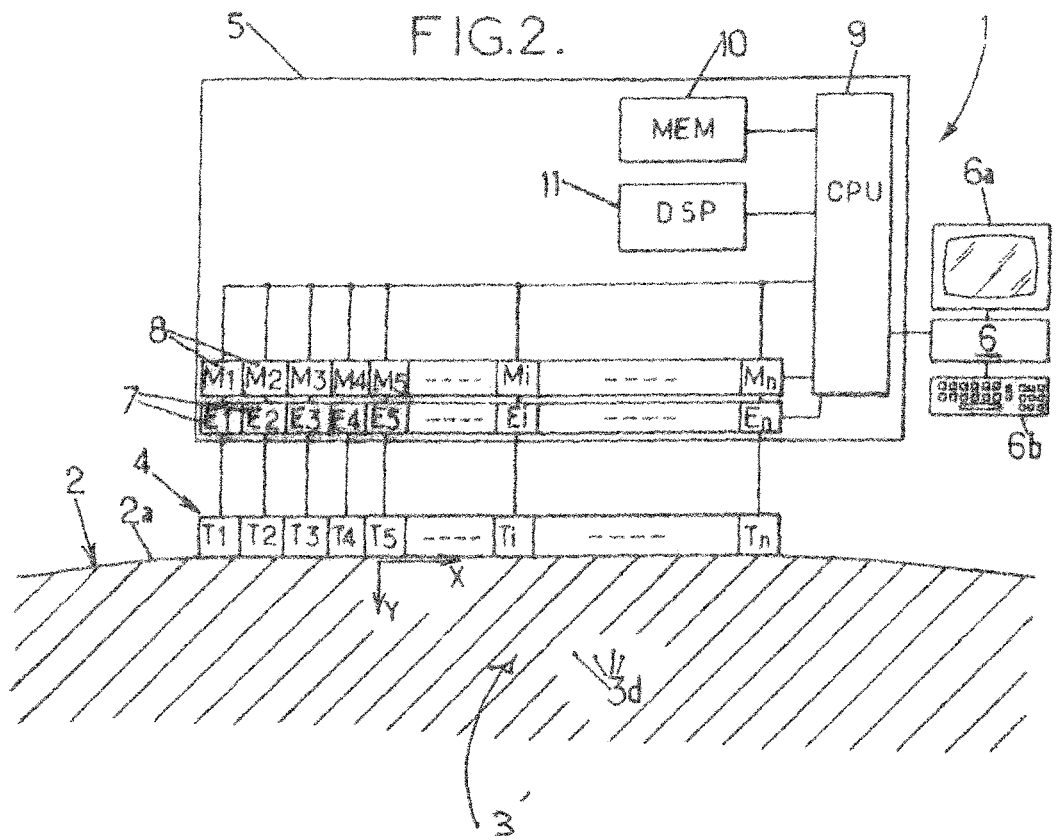
FIG. 2 is a diagrammatic view of a shear-wave imaging device in an embodiment of the second aspect of the invention.

The apparatus 1 of FIG. 2 may include for instance:
- an ultrasound transducer array 4, for instance a linear array typically including n ultrasonic transducers $T_1$-$T_n$ juxtaposed along an axis as already known in usual echographic probes (the array 4 is then adapted to perform a bidimensional (2D) imaging of the observation field in a plane X, Y (where X and Y are two axis linked to the array 4, which are respectively parallel to the longitudinal direction of array 4 and perpendicular to the transducers Ti of the array), but the array 4 could also be a bidimensional array adapted to perform a 3D imaging of the observation field); the number n of transducers is more than 1, for instance a few tens (e.g. 100 to 300); the transducers $T_1$-$T_n$ of the array 4 deliver ultrasound compression wave pulses, which pulses are of the type commonly used in echography, for example having a frequency lying in the range 0.5 MHz to 100 MHz, and preferably in the range 0.5 MHz to 15 MHz, e.g. being about 2.5 MHz;

an electronic bay 5 controlling the transducer array 4 and acquiring signals therefrom;

a microcomputer 6 for controlling the electronic bay 5 and viewing ultrasound images obtained from the electronic bay, said computer 6 including for instance a screen 6a and a keyboard 6b or other user interfaces.

The electronic bay 5 and the microcomputer 6 will be referred herein as the control system of the apparatus 1. Such control system might be constituted of more than two devices, or by one single electronic device could fulfill all the functionalities of the electronic bay 5 and of the microcomputer 6.

The electronic bay 5 may include for instance:

n analog/digital converters 7 ($E_1$-$E_n$) individually connected to the n transducers ($T_1$-$T_n$) of the transducer array 4;

n buffer memories 8 ($M_1$-$M_n$) respectively connected to the n analog/digital converters 7, a central processing unit 9 (CPU) communicating with the buffer memories 8 and the microcomputer 6, a memory 10 (MEM) connected to the central processing unit 8;

a digital signal processor 11 (DSP) connected to the central processing unit 9.

The transducers $T_1$-$T_n$ are controlled independently of one another by the central processing unit 9. The transducers T1-Tn can thus emit selectively:

either an unfocussed ultrasound compression wave;

or else an ultrasound compression wave that is focused on one or more points of the soft tissues 3'.

The wording "unfocussed ultrasound compression wave" as understood herein means any unfocussed wave illuminating the entire observation field in the soft tissues, for instance:

an ultrasound compression wave that is "plane" (i.e. a wave whose wave front is rectilinear in the X,Y plane), or any other type of unfocused wave;

a wave generated by causing random ultrasound signals to be emitted by the various transducers $T_1$-$T_n$;

or an ultrasound compression wave that is focused on one or more points of the soft tissues 3';

or weakly focusing waves (known as "fat" transmit focusing: ratio Focal distance/Aperture>2.5);

or diverging waves such as spherical waves;

or waves focused simultaneously on several focal points;

or more generally any kind of transmit waves that do not correspond to conventional focusing using a single focal point location and a ratio Focal distance/Aperture<2.5.

During operation of the apparatus 1, the transducer array 4 is placed in contact with the skin 2a of the patient 2, over the soft tissue 3' to be studied.

The way of operation of the apparatus 1 is controlled by the control system, i.e. the central processing unit 9 and/or the computer 6, which are programmed for this way of operation.

Observing the Propagation of the Shear Wave

To observe the propagation of the shear wave in the soft tissues 3', the control system 6, 9 of the apparatus 1 is programmed to perform several steps in succession:

a) an excitation step during which the control system 6, 9 causes an elastic shear wave to be generated in the soft tissues 3' by causing at least one ultrasound wave that is focused in the patient's body to be emitted by the array 4 (this focussed wave may be emitted by all or part of the transducers $T_1$-$T_n$);

b) an observation step during which the propagation of the shear wave is observed simultaneously at a multitude of points of the observation field in the soft tissues 3', this observation step comprising the following substeps:

b11) the control system 6, 9 causes the array 4 to emit into the viscoelastic medium a succession of unfocused ultrasound compression waves (these unfocussed waves may be emitted by all or part of the transducers $T_1$-$T_n$) at a rate of at least 300 shots per second, for instance at least 500 shots/s (the focusing and the timing of the focussed ultrasound wave emitted in step a), and the timing of said unfocused ultrasound waves are adapted so that at least some of said unfocused ultrasound waves reach the observation field during the propagation of the shear wave through the observation field);

b2) the control system 6, 9 causes the array 4 to detect ultrasound signals received from patient's body 2 (this detection can be carried out by all or part of the transducers of the array 4), said signals comprising echoes generated by the unfocused ultrasound compression wave interacting with the reflecting particles 3d in the observation field, these echoes corresponding (directly or indirectly) to successive images of the displacement of the viscoelastic medium constituting the soft tissues 3'; the detected signals are recorded in real time in the buffer memories $M_1$-$M_n$;

c) at least one processing step during which:

c1) the control system 6, 9 processes the successive ultrasound signals received from the patient's body 2 during substep b2) in order to determine successive propagation images; and c2) the control system 6, 9 determines at least one movement parameter for the viscoelastic medium constituting the soft tissues 3' at various points in the observation field.

It should be noted that the above substep c2) could be omitted: more generally, the method of the invention does not require determining propagation images, and the control system 6, 9 may determine said movement parameter by any other means.

The focused ultrasound wave emitted during the excitation step a) may be a monochromatic wave of frequency $\underline{f}$ lying in the range 0.5 MHz to 15 MHz, for, example being equal to about 2.5 MHz, which is emitted for a duration of k/f seconds, where $\underline{k}$ is an integer lying in the range 50 to 5000 (e.g. being about 500) and $\underline{f}$ is expressed in Hz. Such a wave may possibly be emitted during a succession of emission periods separated by rest periods, the emission periods following one another at a rate lying in the range 5 to 1000 emissions per second.

In a variant, the focused ultrasound wave emitted during excitation step a) is a linear combination (in particular a sum) of two monochromatic signals of respective frequencies f1 and f2 such that 20 Hz≤|f1−f2|≤1000 Hz, thus producing an amplitude modulated wave having a modulation frequency |f1−f2|.

In addition, the focused ultrasound wave emitted during excitation step a) may optionally be focused simultaneously or otherwise on a plurality of points so that the shear wave as generated presents a desired wave shape (for example it is thus possible to generate a shear wave that is plane, or on the contrary a shear wave that is focused) and illuminates desired zones in the soft tissues 3'.

During step b1), which may last for example 0.1 to 1 s, it is possible to emit unfocused ultrasound compression waves at a rate lying in the range 500 to 10,000 shots per second, and preferably in the range 1000 to 5000 shots per second (with this rate being limited by the go-and-return travel time for the compression wave through the patient's body 2: it is necessary for all of the echoes that are generated by the compression wave to have been received by the probe 6 before a new compression wave is sent).

Each unfocused ultrasound compression wave propagates through the patient's body 2 at a propagation speed that is much higher than that of shear waves (e.g. about 1500 m/s in the human body), and interacts with the reflecting particles 3*d*, thereby generating echoes or other analogous disturbances in the signal that are known in themselves under the name "speckle noise" in the field of echography.

The speckle noise is picked up by the transducers $T_1$-$T_n$, during substep b2), after each shot of an unfocused ultrasound compression wave. The signal $s_{ij}(t)$ as picked up in this way by each transducer $T_i$ after shot No. j is initially sampled at high frequency (e.g. 30 MHz to 100 MHz) and digitized (e.g. on 12 bits) in real time by the analog/digital converter $E_i$ corresponding to transducer $T_i$.

The signal $s_{ij}(t)$ as sampled and digitized in this way is then stored, likewise in real time, in a the buffer memory $M_i$ corresponding to the transducer $T_i$.

By way of example, each memory Mi may present a capacity of about 128 megabytes (MB), and contains all of the signals $s_{ij}(t)$ received in succession for shots j=1 to p.

In deferred time, after all of the signals $s_{ij}(t)$ corresponding to the same propagation of a shear wave have been stored, the central unit 9 processes these signals (or have them processed by another circuit such a summing circuit, or the computer 6 may process the signals itself) using a conventional path-forming step corresponding to substep c1).

This generates signals $S_j(x,y)$ each corresponding to the image of the observation field after shot No. j.

For example, it is possible to determine a signal $S_j(t)$ by the following formula:

$$S_j(t) = \sum_{i=1}^{n} \alpha_i(x, y) \cdot s_{ij}[t(x, y) + d_i(x, y)/V]$$

where:
- $s_{ij}$ is the raw signal perceived by the transducer No. i after ultrasound compression wave shot No. j;
- t(x,y) is the time taken by the ultrasound compression wave to reach the point of the observation field having coordinates (x,y) in the X, Y coordinate system, with t=0 at the beginning of shot No. j;
- $d_i$(x,y) is the distance between the point of the observation field having coordinates (x,y) and transducer No. i, or an approximation to said distance;
- V is the mean propagation speed of ultrasound compression waves in the viscoelastic medium under observation; and
- $\alpha_i$(x,y) is a weighting coefficient taking account of apodization relationships (in practice, in numerous cases, it is possible to assume that $\alpha_i$(x,y)=1).

The above formula applies mutatis mutandis when the observation field is three-dimensional (with a two-dimensional array of transducers), with space coordinates (x,y) being replaced by (x,y,z).

After the optional path-forming step, the central unit 9 stores in the central memory M, the image signals $S_j$(x,y) (or Sj(x) if the image would be in 1 dimension only, or Sj(x,y,z) in case of a 3D image), each corresponding to shot No. j.

These signals may also be stored in the computer 6 if the computer itself performs the image processing.

These images are then processed in deferred time in substep c2) by correlation and advantageously by cross-correlation either in pairs, or preferably with a reference image, as explained in US-B2-U.S. Pat. No. 7,252,004.

The above-mentioned cross-correlation can be performed, for example, in the digital signal processor 11, or it may be programmed in the central unit 9 or in the computer 6.

During this cross-correlation process, a cross-correlation function $<S_j(x,y),S(x,y),S_{j+1}$ is maximized in order to determine the displacement to which each particle 3*c* giving rise to an ultrasound echo has been subjected.

Examples of such cross-correlation calculations are given in US-B2-U.S. Pat. No. 7,252,004.

This produces a set of displacement vectors $\bar{u}(\bar{r},t)$ generated by the shear waves in each position $\bar{r}$ of the vascular wall 3*a* under the effect of the shear wave (these displacement vectors may optionally be reduced to a single component in the example described herein).

This set of displacement vectors is stored in the memory M or in the computer 6 and can be displayed, for example, in particular by means of the screen 4*a* of the computer, in the form of a slow motion picture in which the values of the displacements are illustrated by an optical parameter such as a gray level or a color level.

The propagation differences of the shear wave between zones having different characteristics in the observation field can thus be seen clearly.

The motion picture of shear wave propagation can also be superposed on a conventional echographic image, which can also be generated by the apparatus 1 described above.

Furthermore, it is also possible to calculate, instead of displacements, the deformations of the soft tissues 3' for each of the points in the observation field, i.e. vectors whose components are the derivatives of the displacement vectors respectively relative to the space variables (X and Y coordinates in the example described). These deformation vectors can be used like the displacement vectors for clearly viewing the propagation of the shear wave in the form of a motion picture, and they also present the advantage of eliminating displacements of the transducer array 4 relative to the patient's body 2 under observation.

Determination of the Shear Wave Propagation Parameter

From the displacement or deformation fields, the computer 6 (or more generally the control system 6, 9) can advantageously then compute at least one propagation parameter of the shear wave, either at certain points (at least 1 point) in the observation field as selected by the user acting on the computer 6, or else throughout the observation field, on the basis of the way in which the movement parameter (displacement or deformation) varies over time in the field of observation X, Y (or X, Y, Z with a two-dimensional array of transducers). When the shear wave propagation parameter is computed at several points in the observation field, the computer 6 may then show a map of said parameter in the observation field, on the screen 6*a*.

The propagation parameter of the shear wave that is calculated during sub-step c2) is selected, for example, from amongst: the shear modulus μ, or Young's modulus E=3μ, $$\left(c_S = \sqrt{\frac{E}{3\rho}},\right.$$

where ρ is the density of the tissues), or the shear elasticity $\mu_1$ or the shear viscosity $\mu_2$, as explained in more details in US-B2-U.S. Pat. No. 7,252,004. Such propagation parameter is representative of the elasticity of the soft tissues 3'.

Finally, instead of computing an image of the soft tissues 3' at substep c1) for determining the movement parameter at substep c2), it would be possible to use the method and apparatus described in document WO-A-2008/139 245 for determining locally said movement parameter in one or several predetermined measurement zone in the observation field, for each measurement zone by one corresponding transducer of the transducer array.

Figure 3:
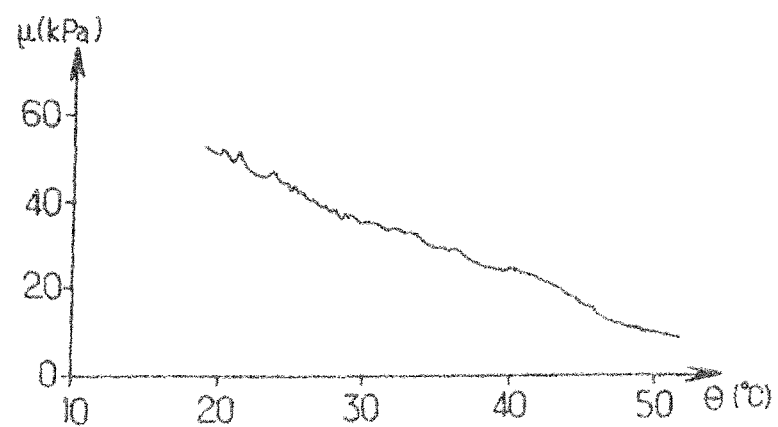
FIG. 3 is an example of a diagram showing the shear modulus μ as a function of the temperature of a mammal soft tissue.

Based on the value of the value of the shear wave propagation parameter computed for one or several points, the computer 6 (or more generally the control system 6,9) determines the temperature of the soft tissues 3' at the corresponding point(s), based on a predetermined law linking said shear wave propagation parameter to said temperature. Such predetermined law can be represented for instance by a diagram as that of FIG. 3 (FIG. 3 corresponds to the case where the shear wave propagation parameter is the shear modulus), which is determined in advance experimentally and memorized in the control system.

Thus, one obtains easily, quickly and non-invasively a measurement of the temperature of the soft tissues. When the temperature is determined in a plurality of points in the observation field, an image of the temperature (indicated for instance by a scale of colors) may be determined and presented to the user on the computer screen 6a. This thermal image may be superposed to an echography of the patient, obtained through the same apparatus 1. The above method works all the more as the shear waves have a relatively high frequency components, e.g. above 50 Hz.

Measuring the temperature in the patient's soft tissues 3' may be useful for instance in view of better controlling local treatments such as thermal treatments, e.g. by focalized ultrasounds (HIFU) or by radio frequency waves (RF ablation).

It should be noted that the temperature as mentioned above may be a difference between first and second temperatures, at two different times. In such a case, the apparatus 1 may deliver a value of a relative temperature, i.e. the value of the variation of temperature between a reference state (e.g. before a thermal treatment) and a current state (e.g. during said thermal treatment).

The invention claimed is:

1. A method for measuring a parameter of non-linearity of elasticity in soft tissue belonging to a cardiovascular wall of a mammal, said method comprising:
   several measurements of a shear wave propagation parameter, at different instants corresponding to different blood pressure values, said shear wave propagation parameter of said soft tissue being measured by using an array of ultrasonic transducers during propagation of at least a shear wave in said soft tissue, said shear wave propagation parameter being selected from shear wave speed, shear modulus μ, Young's modulus E, shear elasticity $\mu_1$ and shear viscosity $\mu_2$, each measurement of shear wave propagation parameter comprising at least one processing step including at least a substep c2) during which:
   c2) at least one movement parameter is determined in an observation field, said movement parameter characterizing movements of reflecting particles in the soft tissue, and a value of said shear wave propagation parameter is determined based on said movement parameter;
   several measurements of blood pressure corresponding respectively to and simultaneously to said measurements of said shear wave propagation parameter,
   a non-linearity determining step wherein the parameter of non-linearity of elasticity is calculated from;
   said several measurements of said shear wave propagation parameter, and
   said several measurements of blood pressure, said parameter of non-linearity of elasticity being indicative of a modification in elasticity of said soft tissue between said different instants corresponding to different blood pressure values; and
   determining a fragility of the cardiovascular wall based on variations of the parameter of non-linearity of elasticity.

2. The method as claimed in claim 1, wherein the shear wave propagation parameter measurement comprises the following steps:
   a) an excitation step during which the shear wave is generated in the soft tissue;
   b) an observation step during which propagation of the shear wave is observed in an observation field in the soft tissue, this observation step comprising the following substeps:
      b1) causing the array of ultrasonic transducers to emit into the soft tissue a succession of ultrasound compression waves, said ultrasound waves having a timing that is adapted so that at least some of said ultrasound waves penetrate into the observation field while the shear wave is propagating in the observation field; and
      b2) causing ultrasound signals received from said observation field to be detected in real time by said array of ultrasonic transducers, said ultrasound signals comprising echoes generated by the ultrasound compression waves interacting with reflecting particles in the soft tissue;
   c) the at least one processing step during which the ultrasound signals received successively from the observation field are used to determine said at least one movement parameter.

3. The method as claimed in claim 2, wherein said processing step c) further includes, before said substep c2) of determining said movement parameter, a further substep c1) in which:
   c1) the ultrasound signals received successively from the observation field during substep b2) are processed in order to determine successive propagation images of the shear wave.

4. The method as claimed in claim 2, wherein at said substep c2), said movement parameter is determined in at least one predetermined measurement zone in the observation field, by one corresponding transducer which belongs to said transducer array.

5. The method as claimed in claim 2, wherein at said substep b1), said ultrasound compression waves are emitted at a rate of at least 300 shots per second.

6. The method as claimed in claim 1, wherein said soft tissue includes a blood vessel, said shear wave propagation parameter is measured in said blood vessel and said blood pressure is a blood pressure in said blood vessel.

7. The method as claimed in claim 6, wherein the blood pressure is measured at a distance from the observation field and then phased to the measurement of the shear wave propagation parameter by taking into account said distance and a pressure wave propagation celerity.

8. The method as claimed in claim 6, wherein the blood pressure is measured at least at two different characteristic phases of the cardiac cycle, and the measurements of the shear wave propagation parameter are carried out at least at two instants corresponding to said two characteristic phases of the cardiac cycle.

9. The method according to claim 8, wherein said two characteristic phases of the cardiac cycle are the instants of maximum blood pressure and the instant of minimum blood pressure.

10. The method as claimed in claim 1, wherein the parameter of non-linearity of elasticity which is determined at the non-linearity determining step d), is the third order shear elastic modulus A.

11. The method as claimed in claim 10, wherein said shear wave propagation parameter which is determined at each shear wave propagation parameter measurement, is the shear modulus $\mu$, and the third order shear elastic modulus A is determined by solving a set of equations corresponding respectively to the several shear wave propagation measures:

$$A = -12\mu_0 \frac{\mu_0 - \mu(t)}{\sigma(t)}$$

where:
t is the instant when the corresponding shear wave propagation parameter measurement is carried out;
$\mu(t)$ is the value of the shear modulus at instant t;
$\mu_0$ is the value of the shear modulus without constraint;
$\sigma(t)$ is a mechanical stress in the soft tissue at instant t parallel to a direction of polarization of the shear wave, determined on the basis of the pressure in the soft tissue at the place of measurement of the shear wave propagation parameter and at instant t.

12. The method as claimed in claim 1, wherein the blood pressure is measured automatically by a pressure sensor, simultaneously to the shear wave propagation parameter measurement.

13. The method according to claim 3, wherein at the non-linearity determining step, the parameter of non-linearity of elasticity is determined at several points of the observation field and a map of said parameter of non-linearity of elasticity in the observation field is determined.

14. An apparatus for measuring a parameter of non-linearity of elasticity in soft tissue belonging to a cardiovascular wall of a mammal, the apparatus comprising at least one electronic control system, and an array of transducers that are controlled independently by said at least one electronic control system, said apparatus being adapted:
to carry out several measurements of a shear wave propagation parameter and of blood pressure, at different instants corresponding to different blood pressure values, said shear wave propagation parameter being measured by using said array of ultrasonic transducers during propagation of at least a shear wave in said soft tissue, said shear wave propagation parameter being selected from shear wave speed, shear modulus $\mu$, Young's modulus E, shear elasticity $\mu_1$ and shear viscosity $\mu_2$, said electronic control system being adapted to determine at least one movement parameter in an observation field and to determine a value of said shear wave propagation parameter based on said movement parameter, said movement parameter characterizing movements of reflecting particles in the soft tissue;
to carry out several measurements of blood pressure corresponding respectively to and simultaneously to said measurements of said shear wave propagation parameter and to calculate a parameter of non-linearity of elasticity of the soft tissue, from:
said several measurements of said shear wave propagation parameter, at different instants corresponding to different blood pressure values,
said corresponding several measurements of blood pressure said parameter of non-linearity of elasticity being indicative of a modification in elasticity of said soft tissue between said different instants corresponding to different blood pressure values; and
determining a fragility of the cardiovascular wall based on variations of the parameter of non-linearity of elasticity.

15. The apparatus according to claim 14, wherein the electronic control system is adapted:
a) to generate the elastic shear wave in the soft tissue;
b) to observe propagation of the shear wave in an observation field in the soft tissue, by:
b1) causing the array of transducers to emit into the medium a succession of ultrasound compression waves, said ultrasound waves having a timing that is adapted so that at least some of said ultrasound waves penetrate into the observation field while the shear wave is propagating in the observation field; and
b2) causing ultrasound signals received from said observation field to be detected in real time by said array of transducers, said ultrasound signals comprising echoes generated by the unfocused ultrasound compression wave interacting with reflecting particles in the medium;
c) to process the ultrasound signals received successively from the observation field to determine said at least one movement parameter.

16. The apparatus according to claim 15, wherein said control system is adapted to determine successive propagation images of the shear wave, and to determine therefrom said movement parameter.

17. The apparatus according to claim 15, wherein said control system is adapted to determine said movement parameter in at least one predetermined measurement zone in the observation field, based on data coming from one corresponding transducer which belongs to the transducer array.

18. The apparatus according to claim 14, wherein the control system is adapted to have said ultrasound compression waves emitted at a rate of at least 300 shots per second.

19. The apparatus according to claim 14, wherein said shear wave propagation parameter which is determined by the control system, is the shear modulus and the control system is adapted to determine the third order shear elastic modulus A by solving a set of equations corresponding respectively to the several shear wave propagation, measures:

$$A = -12\mu_0 \frac{\mu_0 - \mu(t)}{\sigma(t)}$$

where:
t is the instant when the corresponding shear wave propagation parameter measurement is carried out;
$\mu(t)$ is the value of the shear modulus at instant t;
$\mu_0$ is the value of the shear modulus without constraint;
$\sigma(t)$ is a mechanical stress in the soft tissue at instant t parallel to a direction of polarization of the shear wave, determined on the basis of the pressure in the soft tissue at the place of measurement of the shear wave propagation parameter and at instant t.

20. The apparatus according to claim 14, wherein the control system is adapted to measure, blood pressure automatically through a pressure sensor, simultaneously to the shear wave propagation parameter measurement.

21. The apparatus according to claim 14, wherein said soft tissue includes a blood vessel, said shear wave propagation parameter is measured in said blood vessel and said blood pressure is a blood pressure in said blood vessel, and wherein the control system is adapted to phase the measurement of the blood pressure to the measurement of the shear wave propagation parameter by taking into account:
  a distance between a place of measurement of blood pressure and the observation field and then phased said distance,
  and a pressure wave propagation celerity.

22. The apparatus according to claim 14, wherein said soft tissue includes a blood vessel, said shear wave propagation parameter is measured in said blood vessel and said blood pressure is a blood pressure in said blood vessel, and wherein the control system has measures of the blood pressure at least at two different characteristic phases of the cardiac cycle, and is adapted to perform the measurements of the shear wave propagation parameter at least at two instants corresponding to said two characteristic phases of the cardiac cycle.

23. The apparatus according to claim 22, wherein said two characteristic phases of the cardiac cycle are the instants of maximum blood pressure and the instant of minimum blood pressure.

24. The apparatus according to claim 22, wherein the control system is adapted to measure the blood pressure at said characteristic phases of the cardiac cycle.

25. The apparatus according to claim 14, wherein the control system is adapted to determine the parameter of non-linearity of elasticity at several points of the observation field and to determine a map of said parameter of non-linearity of elasticity in the observation field.

\* \* \* \* \*